US010244335B2

United States Patent
Lenarz et al.

(10) Patent No.: US 10,244,335 B2
(45) Date of Patent: Mar. 26, 2019

(54) PRE-LOAD FEEDBACK OF A MIDDLE-EAR COUPLER

(71) Applicant: MED-EL Elektromedizinische Geraete GmbH, Innsbruck (AT)

(72) Inventors: Thomas Lenarz, Hannover (DE); Uwe Steinhardt, Hirrlingen (DE); Daniel Schurzig, Hannover (DE); Max Frölich, Hannover (DE); Kathrin Sonntag, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 147 days.

(21) Appl. No.: 15/470,992

(22) Filed: Mar. 28, 2017

(65) Prior Publication Data

US 2017/0289713 A1   Oct. 5, 2017

Related U.S. Application Data

(60) Provisional application No. 62/314,429, filed on Mar. 29, 2016.

(51) Int. Cl.
*H04R 25/00* (2006.01)
*A61N 1/36* (2006.01)

(52) U.S. Cl.
CPC ....... *H04R 25/606* (2013.01); *A61N 1/36036* (2017.08); *H04R 25/305* (2013.01); *H04R 25/65* (2013.01)

(58) Field of Classification Search
CPC ............... H04R 25/00–25/75; H04R 2225/00–2225/83; H04R 2460/00–2460/17
See application file for complete search history.

(56) References Cited

U.S. PATENT DOCUMENTS

| 4,004,345 A * | 1/1977 | Ely ................ A61C 5/82 433/139 |
| 2001/0031908 A1 | 10/2001 | Buschek et al. |
| 2013/0345495 A1 | 12/2013 | Santek |
| 2015/0045883 A1 | 2/2015 | Scheurer |

OTHER PUBLICATIONS

Triagali et al., Intraoperative adjustments to optimize active middle ear implant performance; Acta Oto-Laryngologica, Jan. 2011, 10 pages.
International Searching Authority, International Search Report—International Application No. PCT/US17/24657, dated Jun. 27, 2017, together with the Written Opinion of the International Searching Authority, 13 pages.

* cited by examiner

*Primary Examiner* — Thaddeus B Cox
(74) *Attorney, Agent, or Firm* — Sunstein Kann Murphy & Timbers LLP (57) ABSTRACT

A coupling device for a middle ear implant includes a transducer end configured to engage an implantable electromechanical transducer, a bone engagement end configured to engage a temporal bone surface of a recipient patient, a planar loading spring located between the transducer end and the bone engagement end and configured for compression by displacement of the transducer end and the bone engagement end in towards each other, and compression indicators configured to provide visual indication of a preload force created on the temporal bone surface by the compression of the loading spring.

16 Claims, 9 Drawing Sheets

PRE-LOAD FEEDBACK OF A MIDDLE-EAR COUPLER

This application claims priority from U.S. Provisional Patent Application 62/314,429, filed Mar. 29, 2016, which is incorporated herein by reference in its entirety.

TECHNICAL FIELD

The present invention relates to medical implants, more specifically to a novel coupling device for a middle ear prosthesis system.

BACKGROUND ART

Figure 1:
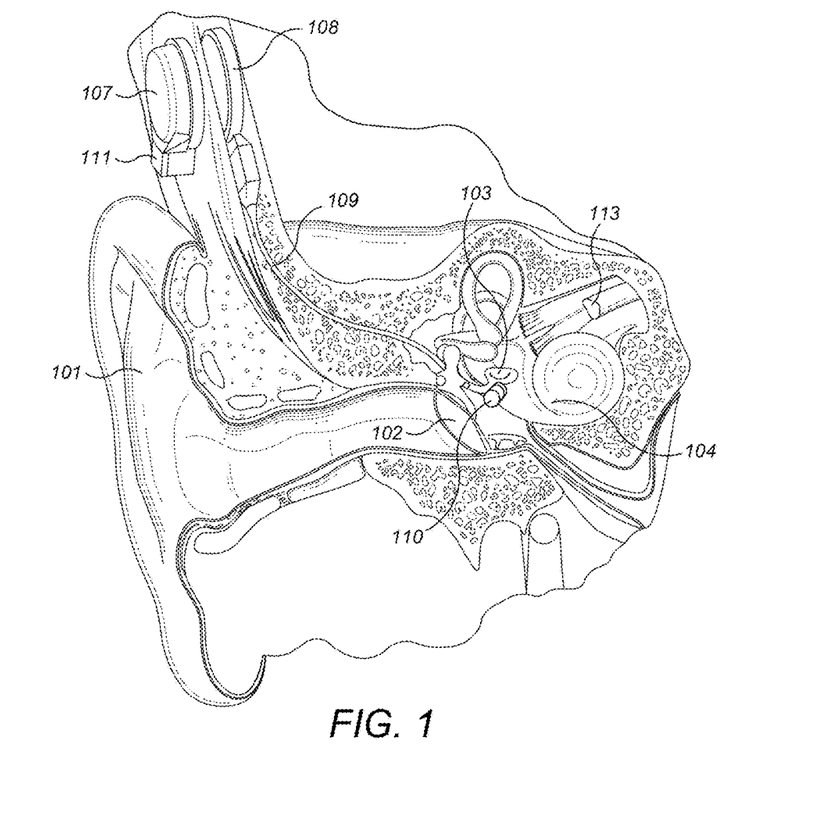
FIG. 1 shows various anatomical structures of a normal human ear with a middle ear implant using a floating mass transducer.

A normal ear transmits sounds as shown in FIG. 1 through the outer ear 101 to the tympanic membrane (eardrum) 102, which moves the ossicles of the middle ear 103 (malleus, incus, and stapes) that vibrate the oval window and round window openings of the cochlea 104. The cochlea 104 is a long narrow organ wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ear's ability to transduce external sounds into meaningful action potentials along the neural substrate of the cochlea 104. To improve impaired hearing, various types of hearing prostheses have been developed. For example, when a hearing impairment is related to the operation of the middle ear 103, a conventional hearing aid or a middle ear implant (MEI) device may be used to provide acoustic-mechanical vibration to the auditory system.

FIG. 1 also shows some components in a typical MEI arrangement where an external audio processor 111 processes ambient sounds to produce an implant communications signal that is transmitted through the skin by an external transmitter 107 to an implanted receiver 108. The receiver 108 includes a receiver coil that transcutaneously receives the implant communications signal which is then demodulated into transducer stimulation signals which are sent by leads 109 through a surgically created channel in the temporal bone to a floating mass transducer (FMT) 110 secured to the incus bone in the middle ear 103. The transducer stimulation signals cause drive coils within the FMT 110 to generate varying magnetic fields which in turn vibrate a magnetic mass suspended within the FMT 110. The vibration of the inertial mass of the magnet within the FMT 110 creates vibration of the housing of the FMT 110 relative to the magnet. This vibration of the FMT 110 is typically coupled to the incus in the middle ear 103 and then to the cochlea 104 and is perceived by the user as sound. See U.S. Pat. No. 6,190,305, which is incorporated herein by reference.

Figure 2:
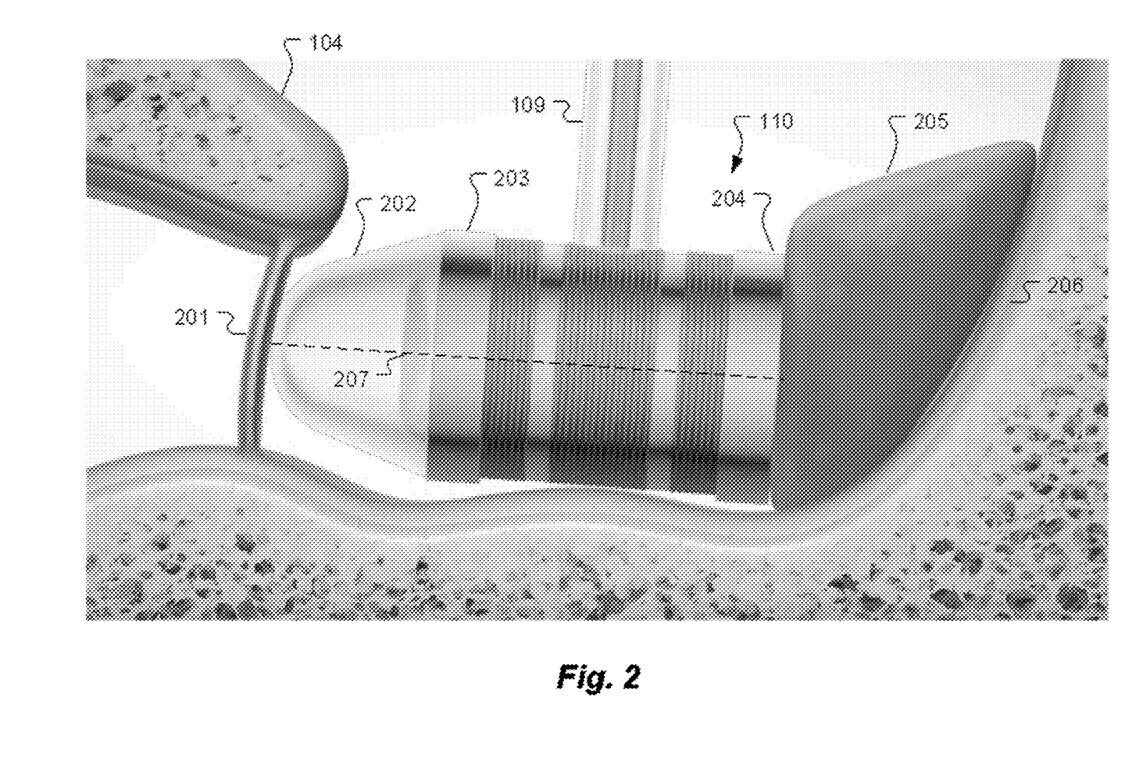
FIG. 2 shows details of coupling a middle ear transducer to a round window membrane according to the prior art.

Alternatively, an engagement member of the FMT 110 can be pushed against the round window membrane of the cochlear outer surface as shown in FIG. 2. The FMT 110 has an inner end 203 and an outer end 204 that are connected by a center axis 207. A conical cochlear engagement member 202 is located at the inner end 203 of the FMT 110 with a cochlear engagement surface that couples the mechanical stimulation signal to the round window membrane 201 in the outer cochlear surface. The FMT 110 is pressed against the round window membrane 201 by a fascia piece 205 made of cartilage that is filled into the space between the FMT 110 and the temporal bone 206 of the middle ear which acts as a fixing anatomical structure. The fascia piece 205 is biocompatible and possesses suitable damping properties for stabilizing the FMT 110 in place against the round window membrane 201 and to prevent it from wandering out of place. But this approach depends very much on the exact execution of the filling of the fascia piece 205, which is manually cut to size by the surgeon and yields non-reproducible results. In addition, exerting too much or too little pressure on the round window membrane 201 can yield a distorted sound percept by the patient. Preliminary studies have shown that the preload force on the FMT 110 should lie between 10 and 20 mN to optimally couple the FMT 110 to the round window membrane 201.

So far, the amount of pre-load force for a middle ear implant has not been standardized. Moreover, the implanting surgeon does not get any feedback information as to the amount of the pre-load force of the coupler to the membrane. In addition, existing middle ear transducer coupling arrangements are not compressible, which would help to place them into position in the middle ear.

U.S. Pat. No. 6,315,710 discloses a middle ear implantable hearing assistance system that provides more precise positioning and contact between a vibrating auditory element and a transducer that senses or provides such mechanical vibrations, such as by providing a controllable, adjustable, or calibrated force. FIGS. 4-7 show different means for these features.

Figure 3:
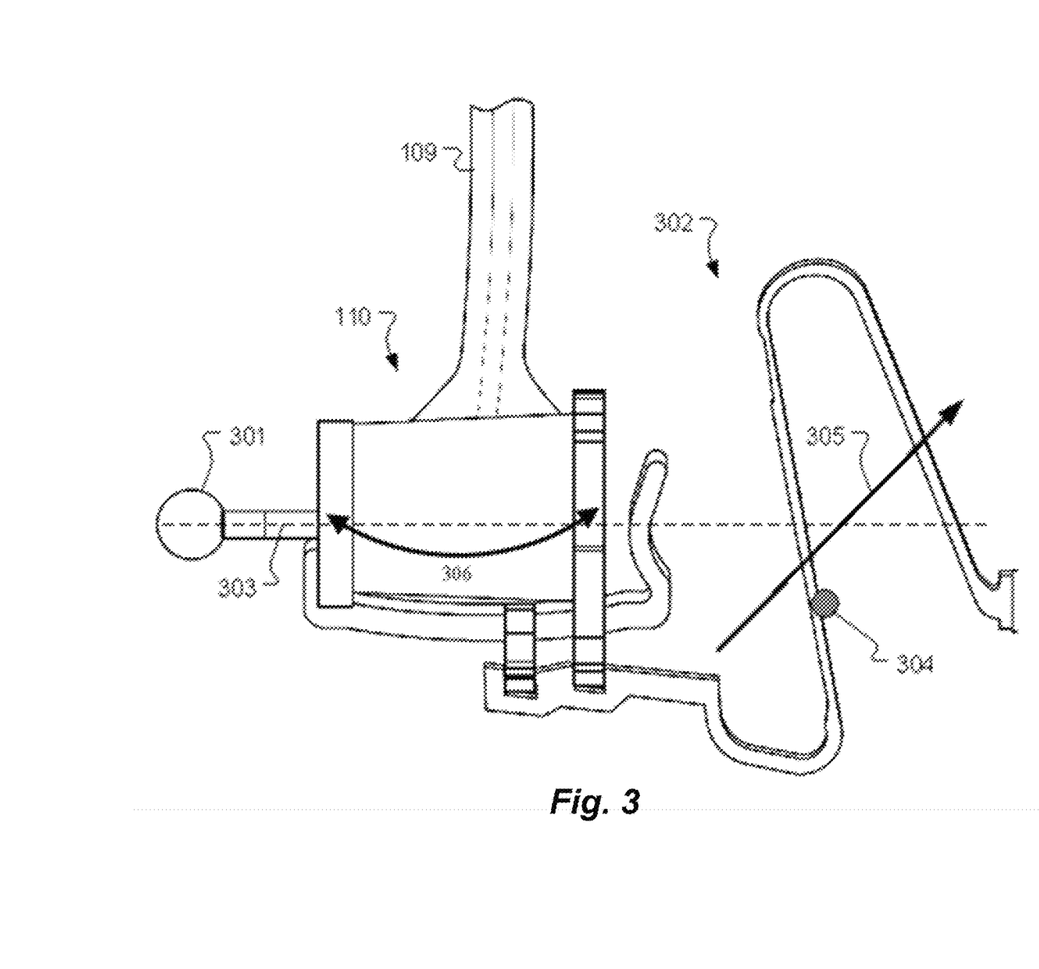
FIG. 3 shows an example of a loading spring according to the prior art.

U.S. Pat. No. 9,191,760 shows a loading spring 302 in the form of an eccentric spring device as shown in FIG. 3, with a center of gravity 304 that is not along the center axis 303 of the FMT 110 and the round window engagement member 301. Furthermore, the structural composition of the spring element results in a pre-load force 305 which is not collinear with the excitation force of the FMT, i.e. the central axis 303 of the FMT 110. Due to these two spring properties, the active FMT 110 will not only move back and forth along its central axis 303, but will also show a rotational component 306 that is offline from the center axis 303. This decreases the vibrational energy introduced into the auditory system by the vibrational oscillations. In this device, the FMT 110 is closer to round window membrane than the loading spring 302 when implanted in the middle ear.

SUMMARY OF THE INVENTION

Embodiments of the present invention are directed to a middle ear implant arrangement with an implantable electromechanical transducer that has opposing ends, which are connected by a center transducer axis. A coupling device includes a transducer end configured to engage the electromechanical transducer, a bone engagement end configured to engage a temporal bone surface of a recipient patient, a planar loading spring located between the transducer end and the bone engagement end of the coupling device and configured for compression by displacement of the transducer end and the bone engagement end in towards each other, and compression indicators configured to provide visual indication of a pre-load force created on the temporal bone surface by the compression of the loading spring.

In further specific embodiments, the coupling device further includes a pair of handling features—e.g., handling holes—in the loading spring configured to engage with a surgical compression tool to create the compression of the loading spring. The transducer end may include a cochlear engagement projection configured to mechanically connect the electromechanical transducer to a cochlear outer membrane surface for delivery of the mechanical stimulation signal to the cochlear outer membrane surface. The loading spring may specifically have an s-shape. The loading spring may be configured for displacement of the transducer end and the bone engagement end of up to 200 µm. The pre-load force may be up to 100 mN; for example, 5-20 mN. The coupling device may be made of nitinol, titanium or gold.

DETAILED DESCRIPTION OF SPECIFIC EMBODIMENTS

Various embodiments of the present invention are directed to a middle ear implant arrangement based on an improved loading spring for a middle ear transducer. The spring is adapted to develop a pre-load force that presses against one end of the electromechanical transducer to firmly engage it against an outer surface of the patient's cochlea (e.g. the round window) with a force that is within a defined range and entirely along the center axis of the transducer, which may also coincide with a central axis of the loading spring. For example, the middle ear transducer may be an FMT 110 as shown in FIGS. 1 and 2 with an inner end 203 and an outer end 204. The ends are connected by a center axis 207, and with a conical cochlear engagement member 202 at the inner end 203 with a cochlear engagement surface that couples the mechanical stimulation signal to the round window membrane 201 in the outer cochlear surface.

Figure 4:
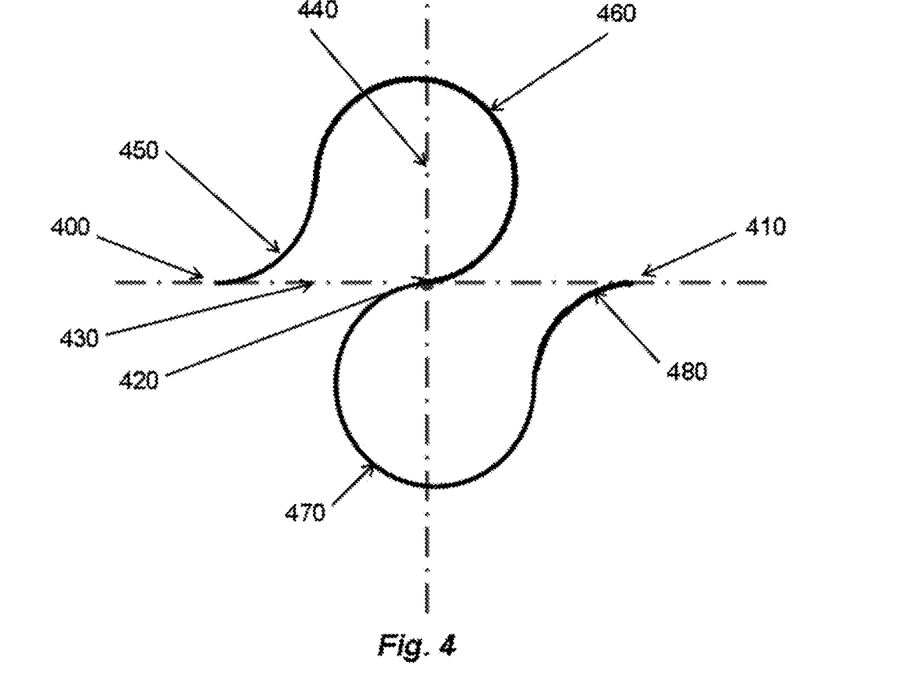
FIG. 4 shows a side view of a loading spring according to an embodiment of the present invention.

FIG. 4 shows one specific embodiment where a loading spring has an inner end 400 that engages the outer end of the transducer, an outer end 410 that engages a fixed anatomical structure within the middle ear of the recipient patient, and a center of mass 420 located on a common line between the inner end 400 and the outer end 410. The loading spring has an s-shape that lies entirely in a two-dimensional plane with a central axis 430 along the common line. The loading spring also is configured for displacement of the inner end 400 and the outer end 410 along the central spring axis 430 so as to fit the loading spring between the transducer and the fixed anatomical structure with a pre-load force that is within a defined range and entirely along the center axis of the transducer and the central spring axis 430. Preferably, this relation is maintained over as long of a displacement range as possible up to 200 µm and more while delivering the desired pre-load force range; for example, a pre-load force of 10-20 mN.

The s-shape of the loading spring also has a symmetry point at the center of mass 420. Applying a pre-load force of up to about 100 mN along the central spring axis 430 substantially maintains the point symmetry, and the absolute value of the curvature along the s-shape is constant. The point symmetry characteristic keeps the center of mass 420 located on the central spring axis 430. The first derivative of the s-shape at the inner end 400 and the outer end 410 is (nearly) zero. The center of mass 420 is an inflection point in the s-shape with a second derivative at or near zero, which also is maintained when applying a pre-load force of up to about 100 mN along the central spring axis 430. More specifically, if the curvature of a first spring section 450 is denoted by some specific value a, the curvature of a second spring section 460 is -a, the curvature of a third spring section 470 is again a, and the curvature of a fourth spring section 480 is again -a. In other words, the loading spring is comprised of a plurality of spring sections having the same absolute values of curvatures.

As previously discussed, a pre-load force of 10-20 mN may be optimal, however, any pre-load force of up to about 100 mN can be applied since the loading spring undergoes uniform deformation over the entire s-shape. The relations between the specific curvatures of the different spring sections may vary by up to about 10%. In particular the relation of the curvatures of all the spring sections of the loading spring is maintained. As a result, no one particular portion of the spring element is more prone to breakage than any other one, and so there is no need to introduce different diameter sections.

The overall spring stiffness can be selected such that a displacement of up to 200 µm or even more can be achieved while ensuring the desired pre-load force of 10-20 mN. The actual relation of the displacement and pre-load force also depends on the thickness of the spring. The overall height of the loading spring may be comparable to the diameter of the cylindrical transducer housing; e.g., about 1.5 mm. This is a convenient feature for manufacturing such a device. The specific values as to applicable pre-load forces and displacements depend on the actual slope of the loading spring around the symmetry point as well as the thickness/diameter of the material used, which may be any biocompatible material such as Nitinol or titanium.

Figure 5:
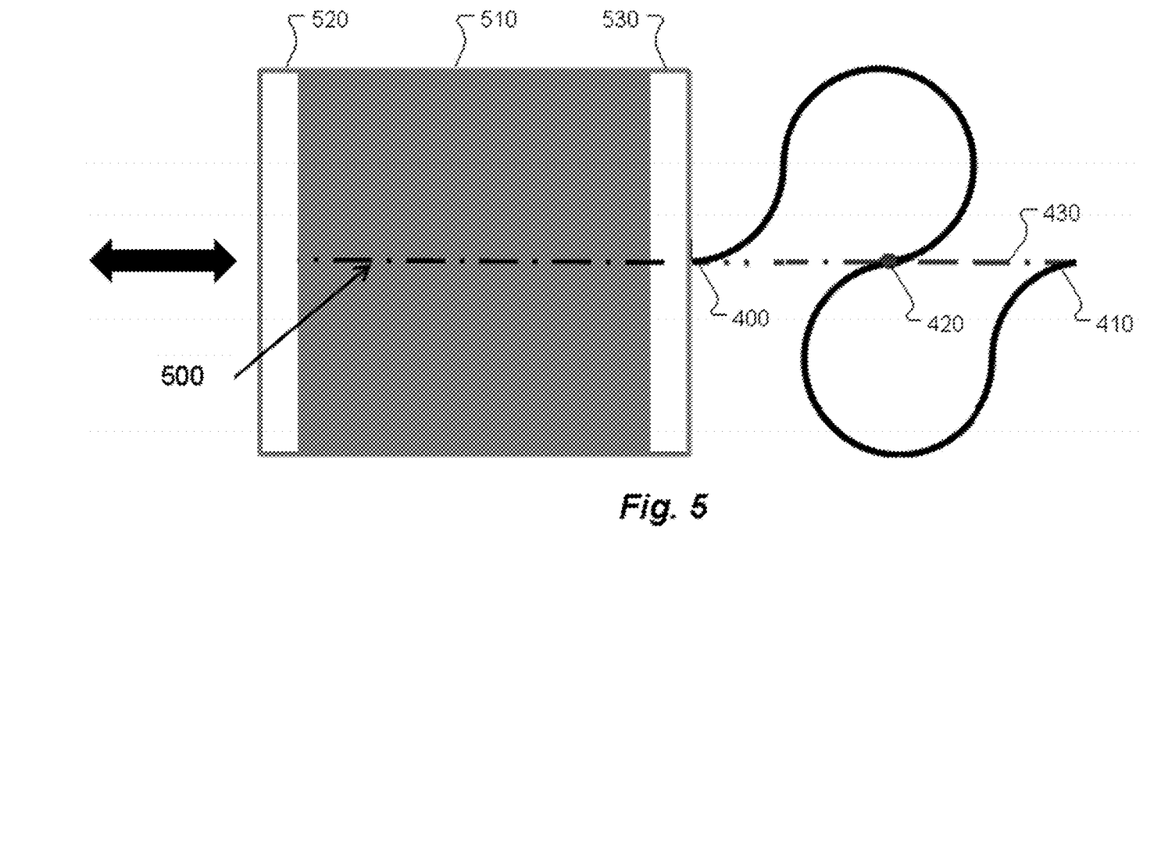
FIG. 5 shows a side view of a loading spring as in FIG. 4 engaged against a middle ear transducer.

FIG. 5 shows a side view of a loading spring as in FIG. 4 which is engaged against a middle ear transducer 510, which has an outer end 530 coupled to the loading device and an inner end 520 directed towards the round window membrane. The inner end 400 of the loading spring is attached (directly or e.g. by means of a coupler element—not shown in the figures) to the outer end 530 of the transducer 510 so that the driving force of the created vibrations acts along the central spring axis 430 and through the center of mass 420 of the loading spring. So if an FMT specifically is used as the transducer 510, then the inner end 400 of the loading spring is attached to the center axis 500 of the cylindrically shaped FMT (which also has a uniform mass distribution around its central axis). At any phase during oscillation of the FMT transducer 510 against the round window membrane, the applied force is along the central spring axis 430 and there is no rotational force component off angle from the axis. So no torque is applied to the transducer 510 or any middle ear anatomical structure because of the alignment of central spring axis 430 and center transducer axis 500.

Embodiments of the present invention also are directed to an improved transducer coupling device for controlling the pre-load force placed on a middle ear membrane during the implantation surgery. Indicator structures on the coupling device give the surgeon visual feedback of the pre-load force. A special compression tool can be used to create the desired pre-load force and to decrease the length of the coupling device to easily place the coupling device into the middle ear in engagement with the middle ear membrane. After placement, the compression tool can be extracted.

Figure 6A:
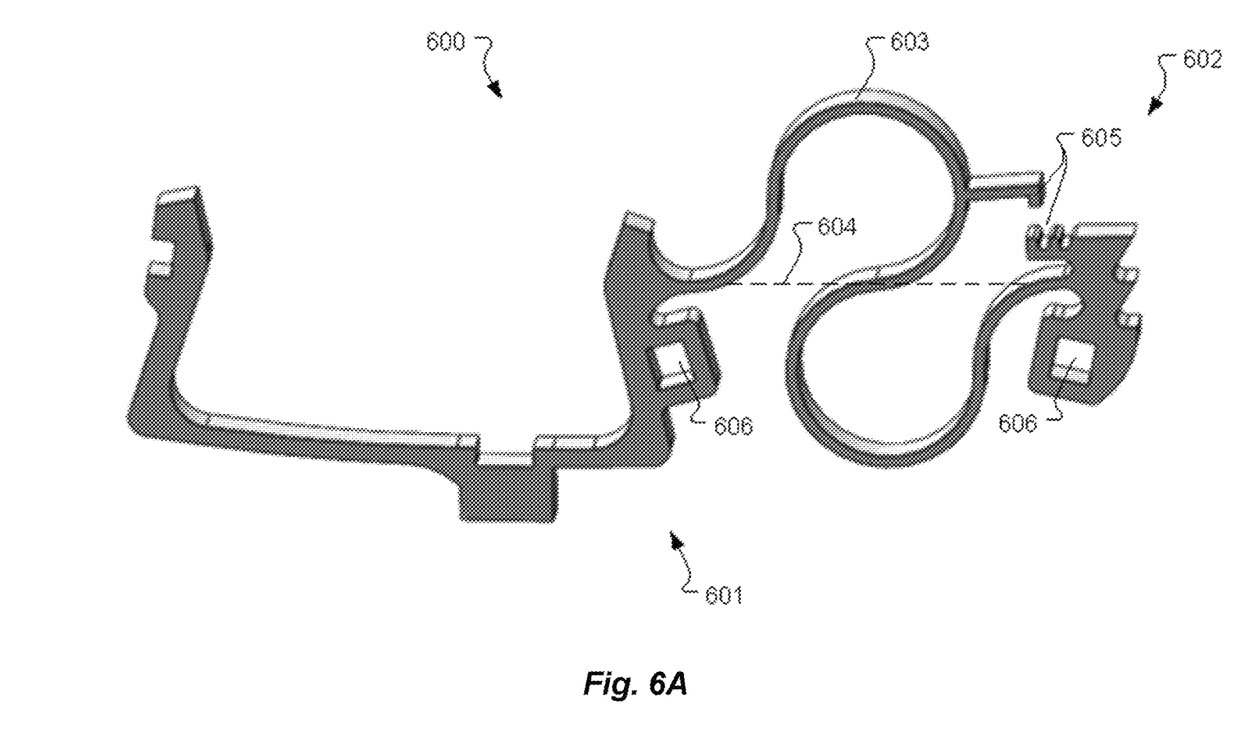
FIG. 6A is an elevated side view of a coupling device for a middle ear implant with pre-load force indicators according to an embodiment of the present invention.
Figure 6B:
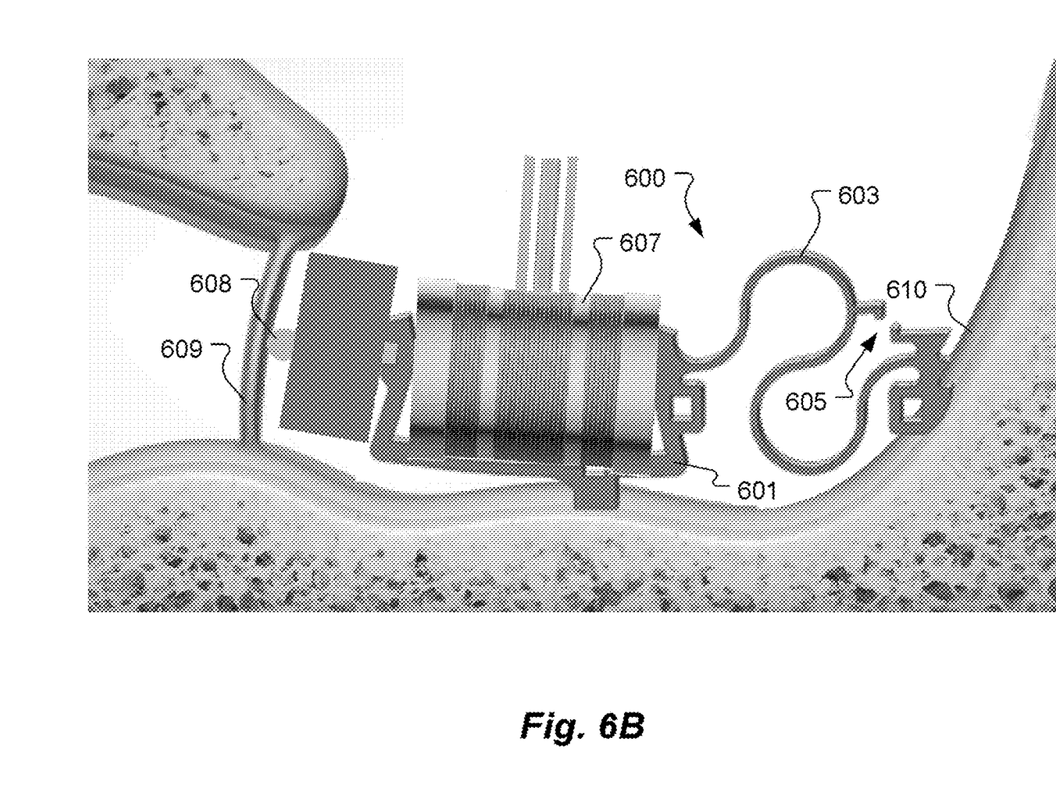
FIG. 6B is a side view of the coupling device of FIG. 6A after implantation into the middle ear with an electromagnetic transducer.

FIG. 6A is an elevated side view of a coupling device for a middle ear implant that includes pre-load force indicators according to an embodiment of the present invention. FIG. 6B is a side view of the coupling device of FIG. 6A after implantation into the middle ear with an electromagnetic transducer. The coupling device 600 includes a transducer end 601 that is configured to engage the electromechanical transducer 607 and a bone engagement end 602 that is configured to engage a temporal bone surface 610 of a recipient patient. The coupling device 600 provides vibratory contact between the electromechanical transducer 607 and a cochlear outer membrane surface such as round window membrane 609. An s-shaped planar loading spring 603 is located between the transducer end 601 and the bone engagement end 602 and is configured for compression by displacement of the transducer end 601 and the bone engagement end 602 in towards each other along a spring axis 604. In specific embodiments, the transducer end 601 further comprises a cochlear engagement projection 608 configured to mechanically connect the electromechanical transducer 607 to the round window membrane surface 610 for delivery of the mechanical stimulation signal from the electromagnetic transducer 607 to the round window membrane surface 610.

The coupling device 600 also includes two or more compression indicators 605 that are configured to provide visual indication (to the surgeon) of the pre-load force created on the temporal bone surface 610 by the compression of the loading spring 603, thus being a measure for the pre-load force. In the embodiment shown, one of the compression indicators 605 is located at the bone engagement end 602 of the loading spring 603 and another one of the compression indicators 605 is located on a curve of the loading spring 603. In other specific embodiments, compression indicators may be provided at other structural locations such as other locations on the loading spring 603. The various small bulges and notches of the compression indicators 605 can improve the quality of the visual feedback element.

Figure 7:
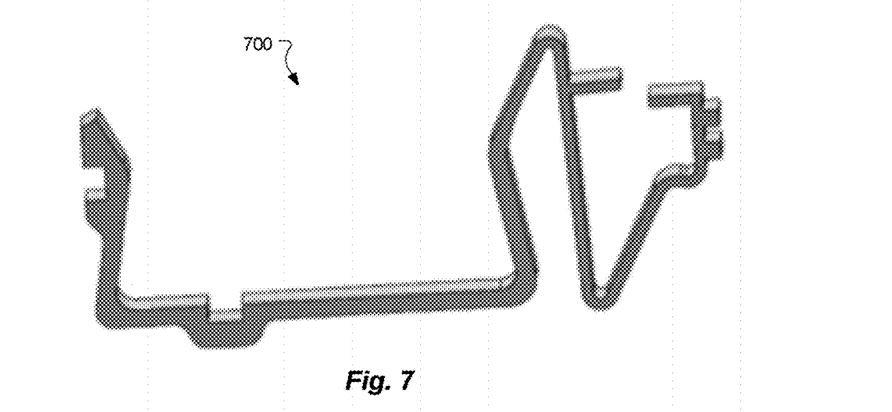
FIG. 7 is an elevated side view of a coupling device for a middle ear implant with pre-load force indicators according to another embodiment of the present invention.
Figure 8:
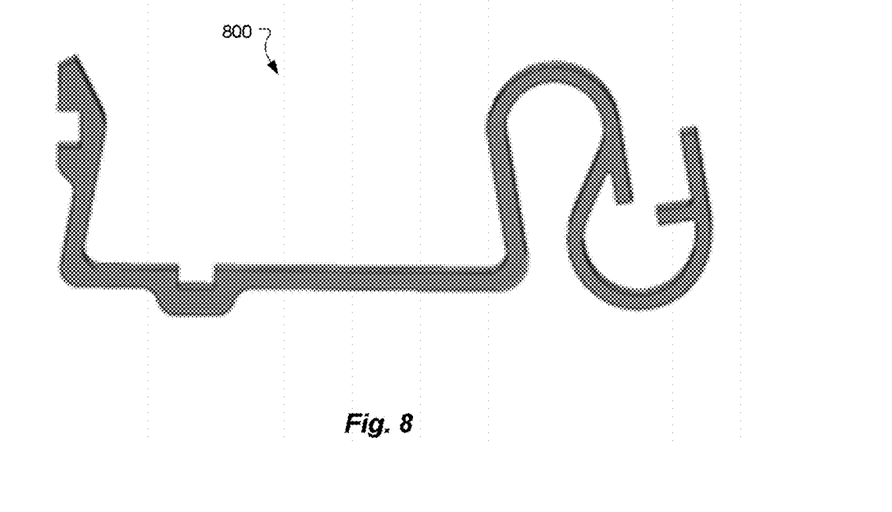
FIG. 8 is a side view of a coupling device for a middle ear implant with pre-load force indicators according to another embodiment of the present invention.

The entire coupling device 600 may lie in a single plane as shown in FIG. 6A, and so may be manufactured from a single piece of a biocompatible metal sheet such as titanium, nitinol or gold. The structure of the coupling device 600 may be cut using mechanical cutting means or laser technology out of such a metal sheet. FIGS. 7 and 8 show side views of other specific possible geometries of coupling devices 700 and 800 according to other specific embodiments.

The loading spring 603 specifically may be configured for displacement of the transducer end 601 and the bone engagement end 602 of up to 200 μm. The pre-load force specifically may be up to 100 mN. For example, in the specific case where the temporal bone surface is the round window membrane, Gostian et al., *Loads and Coupling Modalities Influence the Performance of the Floating Mass Transducer as a Round Window Driver*, Otology & Neurotology 37.5 (2016): 524-532 (incorporated herein by reference in its entirety) has shown that the optimal pre-load force is between 5 and 20 mN.

The thickness of the loading spring 603 typically is in the range of 0.5 mm. Because of this small thickness, there is a risk that the loading spring 603 may be unintentionally bent during the surgical implantation process. Such undesirable bending may be hard for the surgeon to identify because he/she typically only has visual access by looking through the drilled mastoidectomy along a view that is substantially parallel to the longitudinal form of the coupling device 600. Placement of the compression indicators 605 towards the bone engagement end 602 of the loading spring 603 improves the surgeon's chances to identify unintentional bending of the coupling device 600 during implantation, especially if the bending occurs towards the bone engagement end 602, for example, between the locations of the compression indicators 605. For this reason, the compression indicators 605 may be longitudinal members, which may be arranged parallel or orthogonal to each other. Because of the relatively large size of the electromechanical transducer, the surgeon may be unable to see the transducer end 601 of the loading spring 603. Therefore, it may be advantageous if at least one or two compression indicators 605 are at least 2 mm distal to the transducer end 601.

The compression indicators 605 may have a resonance frequency above 10 kHz to avoid displaying unwanted oscillation modes. Such oscillations could create a mechanical excitation which is not axial to the stimulation direction of the electromechanical transducer and so could cause a decrease in efficiency and/or a misplacement of the device over time.

Figure 9:
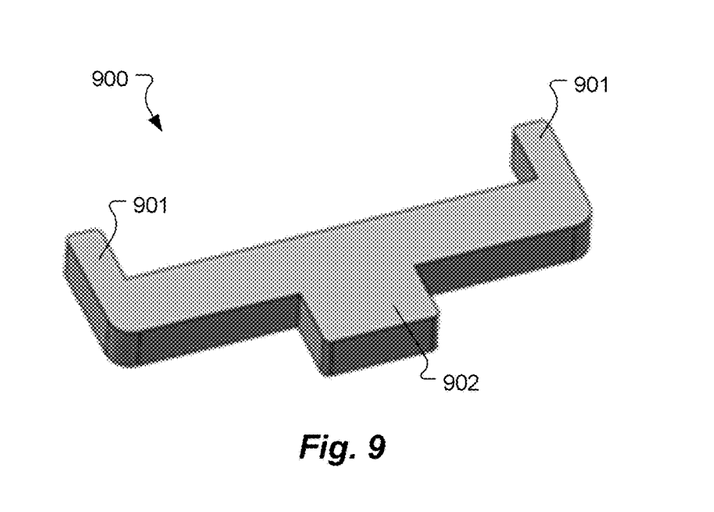
FIG. 9 is an elevated side view of a compression loading tool according to an embodiment of the present invention.
Figure 10:
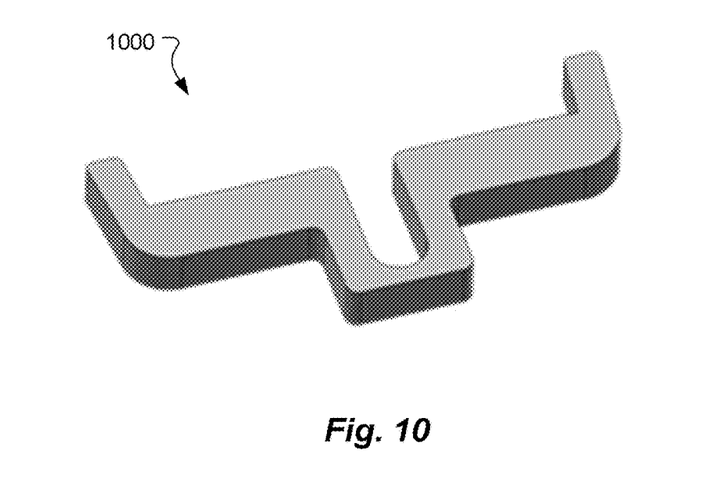
FIG. 10 is an elevated side view of a compression loading tool according to another embodiment of the present invention.

In the specific embodiment shown in FIG. 6A-6B, the coupling device 600 further includes a pair of handling features 606—e.g., handling holes—in the loading spring 603. These handling features 606 are configured to engage with a surgical compression tool to create the compression of the loading spring 603. For example, FIGS. 9 and 10 show elevated side views of specific embodiments of such a compression loading tool 900 and 1000. The end projections 901 are configured to fit into the holes of the handling features 606 so as to create the desired amount of spring compression and pre-load force. The center handling projection 902 allows the compression loading tool 900/1000 to be grasped by a surgical handling tool such as tweezers or forceps to allow the surgeon to conveniently position the transducer and coupling device in the desired position in the middle ear.

The foregoing discussion applies to all specific types of middle ear prostheses that couple an output driver part of an active or passive implant system to a membrane which closes a natural or artificial window in the cochlea, in the vestibulum, or in the labyrinth (equilibrium organ).

Although various exemplary embodiments of the invention have been disclosed, it should be apparent to those skilled in the art that various changes and modifications can be made which will achieve some of the advantages of the invention without departing from the true scope of the invention.

What is claimed is:

1. A middle ear implant arrangement comprising:
   an implantable electromechanical transducer configured to convert an input electrical stimulation signal into a corresponding output mechanical stimulation signal; and
   a coupling device having:
   i. a transducer end configured to engage the electromechanical transducer,
   ii. a bone engagement end configured to engage a temporal bone surface of a recipient patient;
   iii. an s-shape planar loading spring having a central spring axis along a common line between the transducer end and the bone engagement end and a center of mass located on the common line, wherein the loading spring is configured for compression along the central spring axis by displacement of the transducer end and the bone engagement end in towards each other; and
   iv. a plurality of compression indicators configured to provide visual indication of a pre-load force created on the temporal bone surface by the compression of the loading spring.

2. The middle ear implant arrangement according to claim 1, further comprising:
   a pair of handling features in the loading spring configured to engage with a surgical compression tool to create the compression of the loading spring.

3. The middle ear implant arrangement according to claim 2, wherein the handling features are handling holes in the loading spring.

4. The middle ear implant arrangement according to claim 1, wherein the transducer end further comprises a cochlear engagement projection configured to mechanically connect the electromechanical transducer to a cochlear outer membrane surface for delivery of the mechanical stimulation signal to the cochlear outer membrane surface.

5. The middle ear implant arrangement according to claim 1, wherein the loading spring is configured for displacement of the transducer end and the bone engagement end of up to 200 μm.

6. The middle ear implant arrangement according to claim 1, wherein the pre-load force is up to 100 mN.

7. The middle ear implant arrangement according to claim 1, wherein the pre-load force is 5-20 mN.

8. The middle ear implant arrangement according to claim 1, wherein the coupling device is made of nitinol, titanium or gold.

9. A coupling device for a middle ear implant comprising:
   a transducer end configured to engage an implantable electromechanical transducer,
   a bone engagement end configured to engage a temporal bone surface of a recipient patient;
   an s-shape planar loading spring having a central spring axis along a common line between the transducer end and the bone engagement end and a center of mass located on the common line, wherein the loading spring is configured for compression by displacement along the central spring axis of the transducer end and the bone engagement end in towards each other; and
   a plurality of compression indicators configured to provide visual indication of a pre-load force created on the temporal bone surface by the compression of the loading spring.

10. The coupling device according to claim 9, further comprising:
    a pair of handling features in the loading spring configured to engage with a surgical compression tool to create the compression of the loading spring.

11. The coupling device according to claim 10, wherein the handling features are handling holes in the loading spring.

12. The coupling device according to claim 10, wherein the transducer end further comprises a cochlear engagement projection configured to mechanically connect the electromechanical transducer to a cochlear outer membrane surface for delivery of the mechanical stimulation signal to the cochlear outer membrane surface.

13. The coupling device according to claim 9, wherein the loading spring is configured for displacement of the transducer end and the bone engagement end of up to 200 μm.

14. The coupling device according to claim 9, wherein the pre-load force is up to 100 mN.

15. The coupling device according to claim 9, wherein the pre-load force is 5-20 mN.

16. The coupling device according to claim 9, wherein the coupling device is made of nitinol, titanium or gold.

* * * * *